United States Patent
Castellano et al.

(10) Patent No.: US 7,935,250 B2
(45) Date of Patent: May 3, 2011

(54) BLOOD PROCESSING APPARATUS

(75) Inventors: Michele Castellano, Modena (IT); Marco Zanini, Mirandola (IT)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 12/373,855

(22) PCT Filed: Jul. 14, 2006

(86) PCT No.: PCT/IB2006/001943
§ 371 (c)(1), (2), (4) Date: Apr. 14, 2009

(87) PCT Pub. No.: WO2008/010004
PCT Pub. Date: Jan. 24, 2008

(65) Prior Publication Data
US 2009/0284108 A1    Nov. 19, 2009

(51) Int. Cl.
*B01D 35/00* (2006.01)
*A61B 19/02* (2006.01)
(52) U.S. Cl. ......... 210/143; 312/209; 210/767; 210/646
(58) Field of Classification Search .................. 312/209; 248/183.2
See application file for complete search history.

(56) References Cited

U.S. PATENT DOCUMENTS

| | | | |
|---|---|---|---|
| 2,545,515 A * | 3/1951 | Mast et al. | 108/138 |
| 4,437,638 A | 3/1984 | Scheibenpflug | |
| 5,568,362 A * | 10/1996 | Hansson | 361/736 |
| 5,569,895 A * | 10/1996 | Lynch et al. | 235/1 R |
| 5,769,811 A | 6/1998 | Stacey et al. | |
| 6,143,181 A | 11/2000 | Falkvall et al. | |
| 6,146,523 A | 11/2000 | Kenley et al. | |
| 2002/0147423 A1 | 10/2002 | Burbank et al. | |
| 2004/0195482 A1* | 10/2004 | Kollar et al. | 248/282.1 |
| 2006/0084906 A1 | 4/2006 | Burbank et al. | |
| 2006/0226327 A1* | 10/2006 | Chih | 248/422 |

FOREIGN PATENT DOCUMENTS

| EP | 0 771 569 A2 | 5/1997 |
|---|---|---|
| WO | 2005/074807 A1 | 8/2005 |

\* cited by examiner

*Primary Examiner* — Krishnan S Menon
*Assistant Examiner* — Allison Gionta
(74) *Attorney, Agent, or Firm* — Pearne & Gordon LLP

(57) ABSTRACT

The invention relates to blood processing apparatus comprising a cabinet (2) defining at least an interior housing (6) and presenting an aperture (6a) for allowing access from outside into said housing. The apparatus has a user interface (13) mounted in a movable manner on the cabinet between at least a first position, where the user interface is adjacent to the cabinet in correspondence of said aperture, and a second position, where the user interface is spaced apart from the aperture and opens the access to said housing.

30 Claims, 7 Drawing Sheets

BLOOD PROCESSING APPARATUS

FIELD OF THE INVENTION

The invention relates a blood processing apparatus having an improved cabinet structure.

BACKGROUND OF THE INVENTION

Blood processing apparatus such as extracorporeal blood treatment machines (ultrafiltration machines, hemodialysis machines, hemofiltration machines, hemodiafiltration machines) or apparatus for handling whole blood or blood components comprise a cabinet structure which is used to support the fluid lines, the control systems and a user interface. The user interface can include hardware keys, one or more screens a touch sensitive display and is normally associated to a front panel of the cabinet in order to let the user enter data and/or read machine generated information.

U.S. Pat. No. 6,143,181 discloses a dialysis machine for alternatively hospital care and self-care having a touch screen which can be adjusted universally and to a desired vertical position on the dialysis machine and can be locked in the desired adjusted position. In detail, the adjustable touch screen is pivotally supported by an arm end having a bracket at its opposite end; the bracket can be displaced on a vertical guide provided on the machine, and can be locked in the desired displaced position. The bracket can also be rotated on the vertical guide and can be locked in the desired rotated position. As a consequence, the touch screen can be arrested in a position in relation to the position of the person controlling the dialysis machine which allows the touch screen to be comfortably reached irrespective of the position of said person.

U.S. Pat. No. 6,146,523 discloses a dialysis machine comprising a cabinet enclosing hydraulic circuitry, an extracorporeal circuit module contained in an enclosure that is rotatably mounted to said cabinet, and an elongate arm having a proximal end rotatably connected to the cabinet or to the extracorporeal circuit enclosure. The arm distal end has a user interface having a screen display, said user interface allowing patient or treatment information to be entered into a computer control system for said dialysis machine. The proximal end is capable of rotation with respect to either said cabinet or said extracorporeal circuit enclosure and the user interface is mounted to the distal end of said arm in a manner such that said user interface may be rotated about at least one horizontal axis and about at least one vertical axis to thereby orient said screen display in a multitude of different positions relative to the distal end of said arm.

SUMMARY OF THE INVENTION

The above known solutions have provided mobile user interfaces in order to ease access to the user interface irrespective of the height and position of the user.

However, according to the technical solutions of the prior art, the user interface is supported on a structure separate from the rest of the cabinet and its mobility gives no benefit other than providing the user with an easy to access tool.

Known solutions leave the user freedom to move the user interface in any position, i.e. also in those positions which could interfere with the blood tubing set or which could bother other users or personnel particularly where a number of machines are installed in the same room.

Moreover known mobile user interfaces are mounted on a structure independent from the rest of the machine cabinet, thereby increasing complexity and costs.

In view of this situation it is a goal of the present invention to provide an apparatus with an enhanced cabinet structure with a mobile user interface.

It is a further object of the invention an apparatus where the user interface mobility does not affect the cabinet complexity.

An additional object of the invention is an apparatus where the user interface mobility enhances accessibility and data entry without risk of interfering with other components associated to the apparatus.

The above aims are reached by a blood processing apparatus according to the appended claims. Further characteristics and advantages will better emerge from the following description in relation to some preferred but non-exclusive embodiments of an apparatus according to the invention.

SHORT DESCRIPTION OF THE DRAWINGS

The description will be made with reference to the figures of the accompanying drawings, provided by way of non-limiting example, in which.

DETAILED DESCRIPTION

With reference to the enclosed figures, reference numeral 1 indicates a blood processing apparatus according to an embodiment of the present invention. The blood processing apparatus 1 can be an extracorporeal blood treatment machine for the treatment of pathologies such as kidney failure, liver failure, congestive heart failure, etcetera or a machine for processing whole blood or blood components coming from a donor or from a source (such as one or more containers).

In the embodiment of the attached figures the apparatus 1 is an extracorporeal blood treatment machine for treatment of renal or liver insufficiency (i.e. a machine able to run one or more of the following extracorporeal blood treatments: ultrafiltration, dialysis, hemofiltration, hemodiafiltration).

The apparatus 1 comprises a cabinet 2 presenting a base portion 3, a main body 4 vertically extending from said base, and a top portion 5 extending above said intermediate body. At least a portion of the cabinet has a box-like structure for hosting one or more components of the apparatus.

The cabinet defines an interior housing 6, which could be divided into several areas, wherein a significant part of the hydraulic and electronic components of the apparatus are hosted.

More in detail, referring to the embodiment of the enclosed figures, the apparatus comprises a control system and a power supply system located in said interior housing. More precisely the control system includes one or more electronic cards which are housed in a top portion 6a of the housing 6. Also the power supply system is positioned in correspondence of the top portion of the cabinet in a position near the electronic circuitry. The apparatus 1 also has a hydraulic circuit for the preparation of liquid to be used by the apparatus (dialysis liquid or replacement fluid) and for the discharge of waste liquid. The hydraulic circuit is positioned in the housing 6 below the control system circuitry so that leakages from the hydraulic circuit do not affect the electric or electronic circuitry of the control system. Depending upon design choice, the absolute and relative positions of the hydraulic circuit and of the control system could be different from the one specifically described. The cabinet presents at least an access, for instance on the rear part of the apparatus main body for inspecting said interior housing. This access can be defined by a rear door or by a rear removable panel 7, which can be opened or removed to provide an access to the hydraulic circuit for inspection and service. Of course the access could be defined in correspondence of one side or of the front of the cabinet main body.

In correspondence of a front part of the main body at least one or more pumps 8 (in the enclosed two peristaltic pumps are provided) are located. This pump(s) is designed to cooperate with a corresponding disposable set 9 (which is shown only in part in the enclosed drawings as its structure is not relevant for the purpose of describing the present invention). The cabinet 2 of the exemplifying embodiment presents an aperture 10 located in correspondence of the top portion 5 of the cabinet and allowing access to the top portion 6a of the housing 6, where at least the electronic circuitry 11 of the control system is located. A user interface 13 is movably mounted on the cabinet 2 and is movable from at least a first position, where the user interface 13 is adjacent to the cabinet and closes said aperture 10, and a second position, where the user interface is spaced apart from the aperture and opens the access into said housing. During movement of the user interface at least part of the electronic circuitry does not move as it is fixed to the cabinet.

In the enclosed embodiment the apparatus is an extracorporeal blood treatment machine and the user interface comprises a display screen 100, for instance a touch screen, mounted on a support body 101 of the user interface; the user interface can also comprise a number of hard-keys and/or toggles and or knobs, globally indicated with reference number 102, placed in proximity to the display screen and allowing, in cooperation with the touch screen, to enter or modify parameter values relating to the machine or to the process or treatment delivered by the machine. Of course depending upon the apparatus design the user interface can be different: for instance the display screen could be a normal non touch sensitive screen and the data entry obtained with hardware keys or toggles or knobs.

The support body 101 of the enclosed embodiment presents an L-shaped profile and comprises a first portion 103 receiving the display screen and a second portion, transversal to the first portion 104, defining a receptacle area 105 on an upper side thereof for receiving a tray or other items. The receptacle includes a base wall 105a and side walls 105b emerging from wall 105a. The support body also present sides 106 designed to interact with the cabinet as it will hereinafter be described in grater detail.

Figure 1:
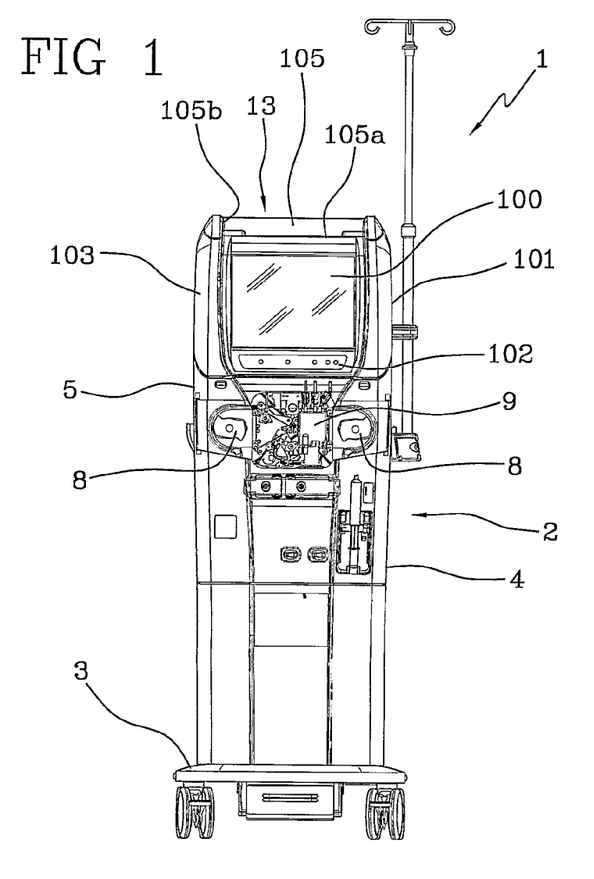
FIG. 1 is a front elevation of a blood processing apparatus according to the invention where the user interface is in a first position.
Figure 2:
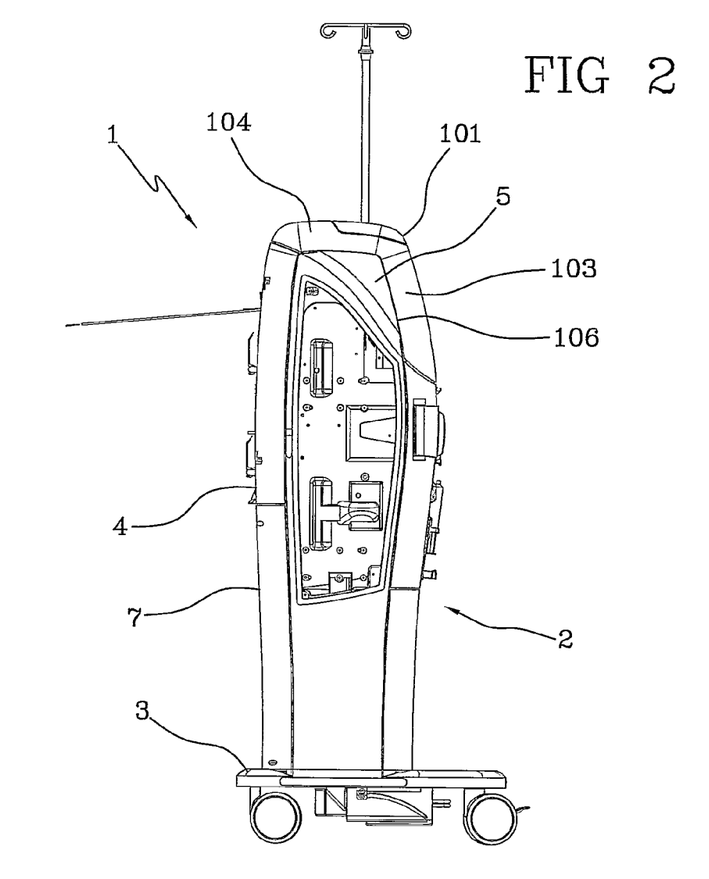
FIG. 2 is a side elevation of the apparatus of FIG. 1.
Figure 3:
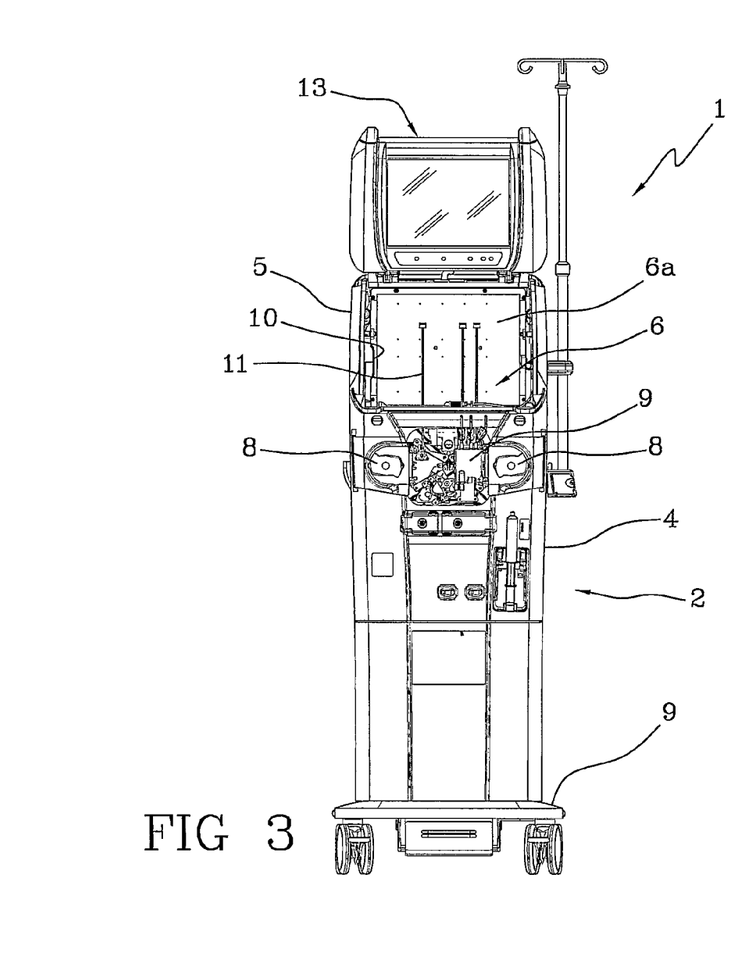
FIG. 3 is a front elevation of a blood processing apparatus according to the invention where the user interface is in a second position.
Figure 4:
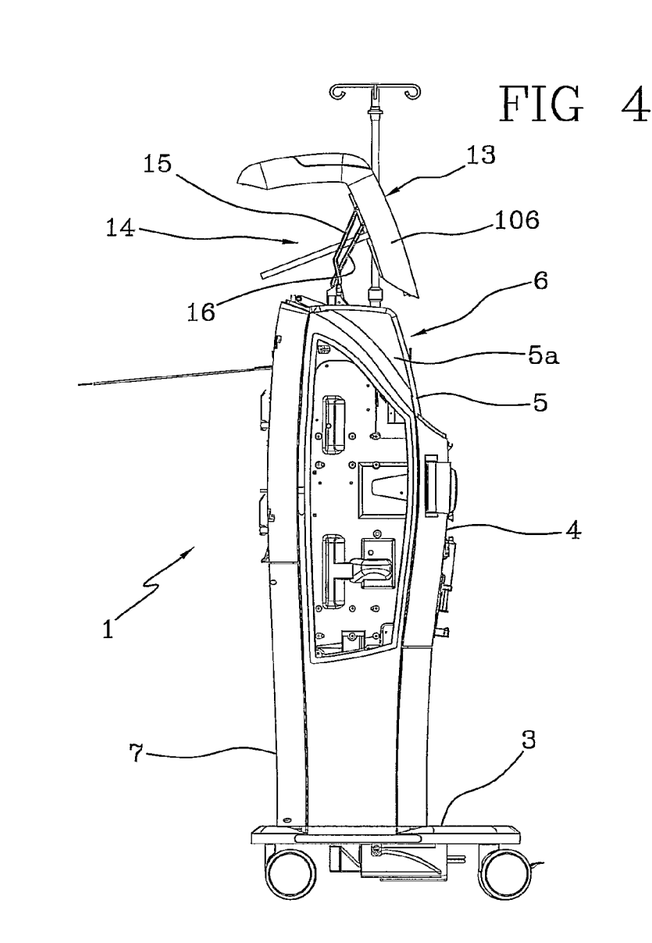
FIG. 4 is a side elevation of the apparatus of FIG. 3.
Figure 5:
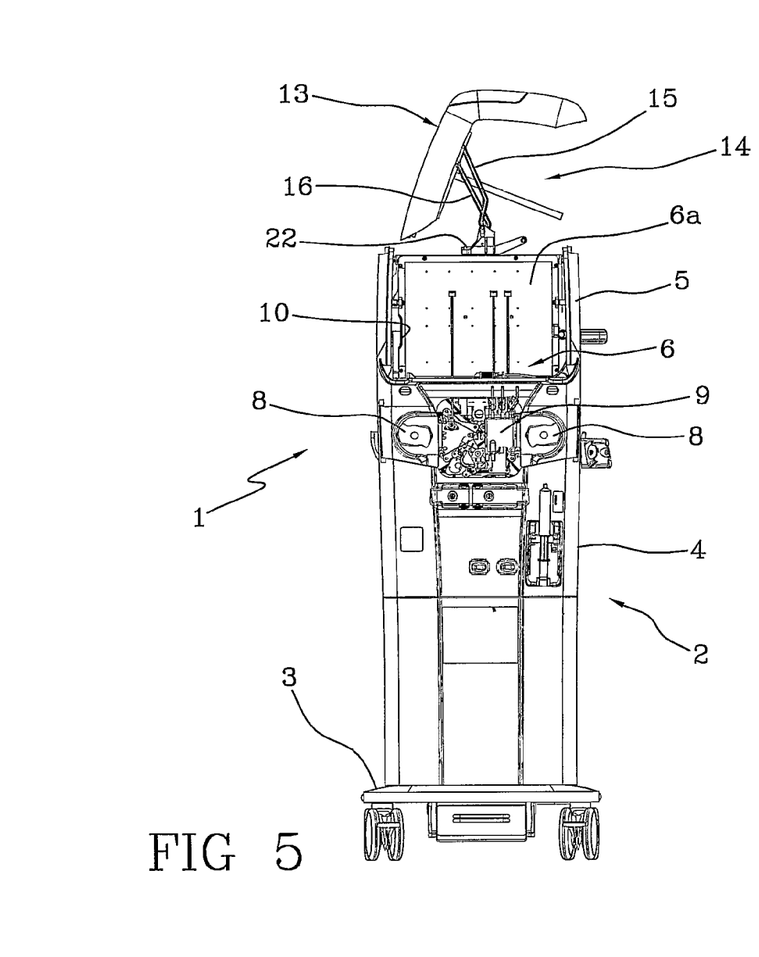
FIG. 5 is a front elevation of a blood processing apparatus according to the invention where the user interface is in a position rotated by 90° with respect to the second position of FIG. 3.
Figure 6:
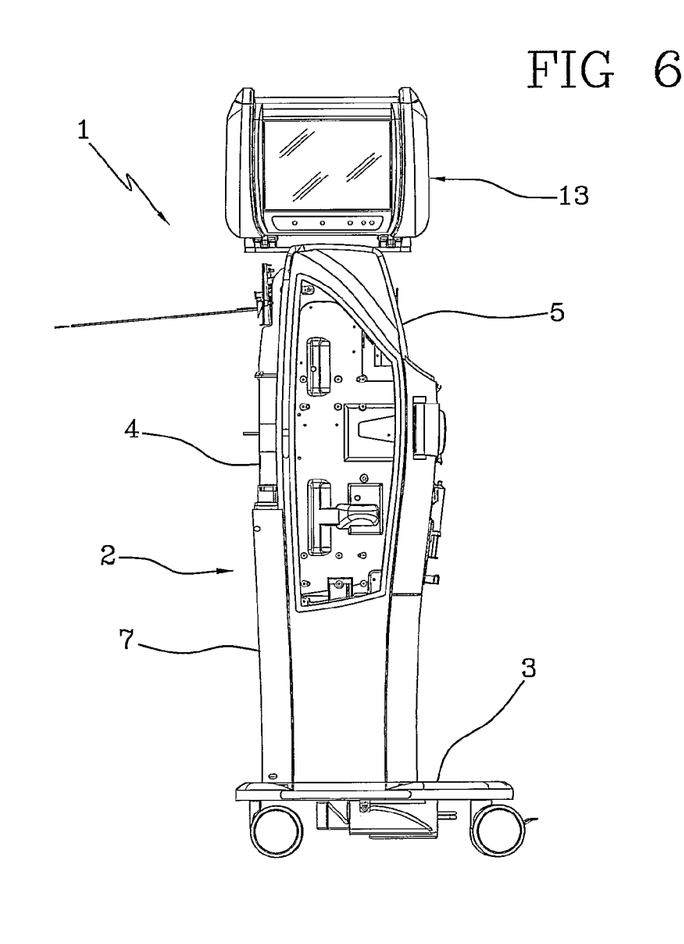
FIG. 6 is a side elevation of the apparatus of FIG. 5.
Figure 7:
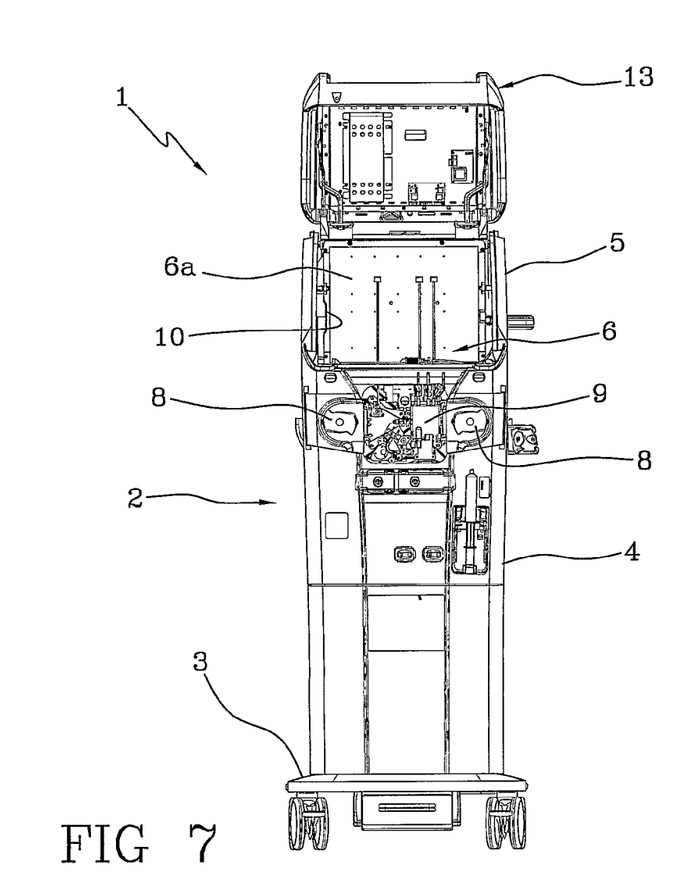
FIG. 7 is a front elevation of a blood processing apparatus according to the invention where the user interface is in a third position rotated by 180° with respect to the second position of FIG. 3.
Figure 8:
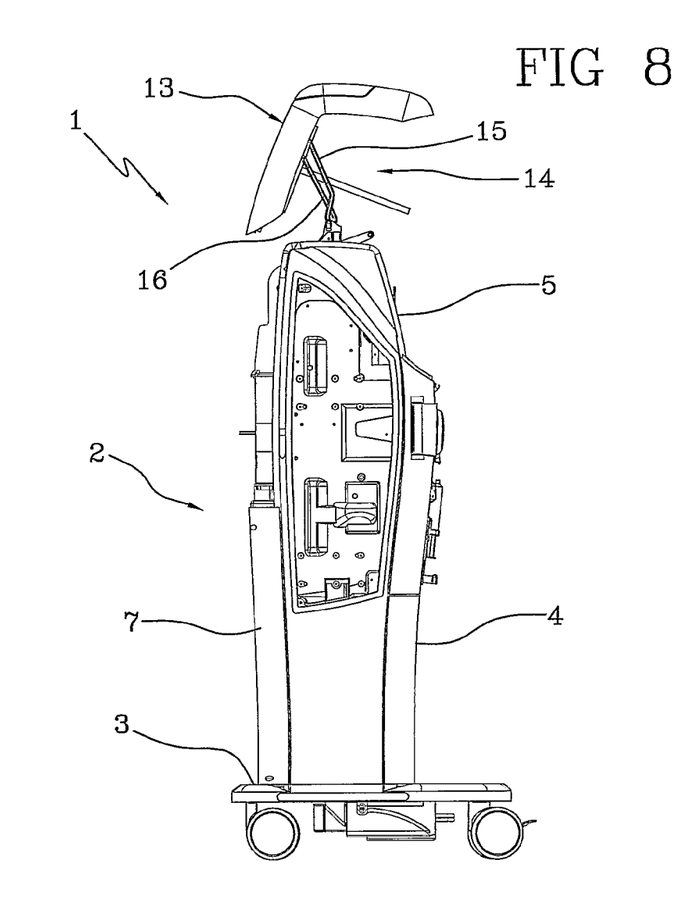
FIG. 8 is a side elevation of the apparatus of FIG. 7.
Figure 9:
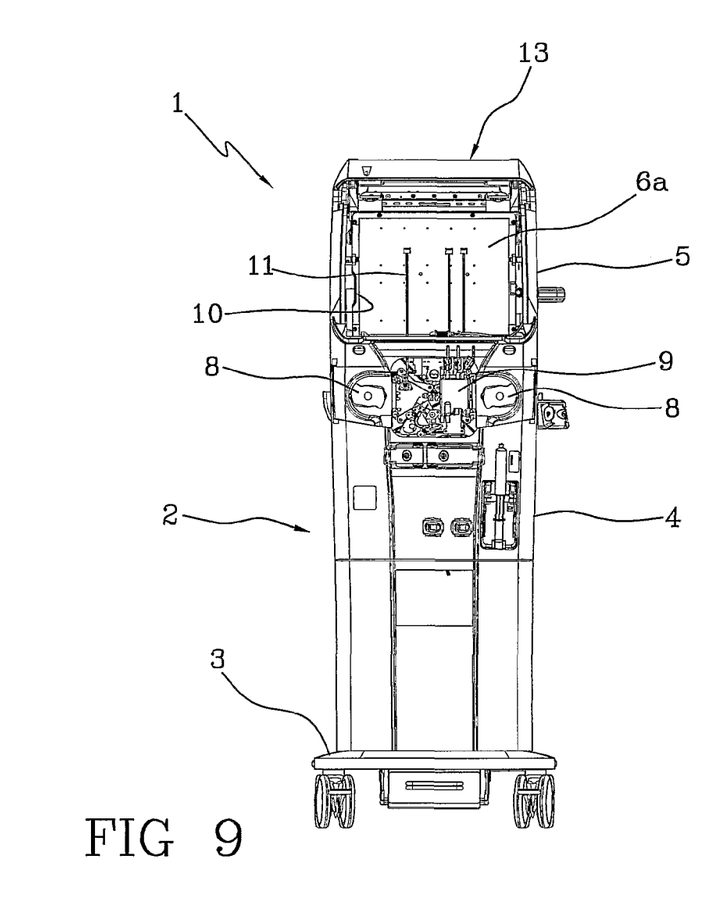
FIG. 9 is a front elevation of a blood processing apparatus according to the invention where the user interface is in a fourth position.
Figure 10:
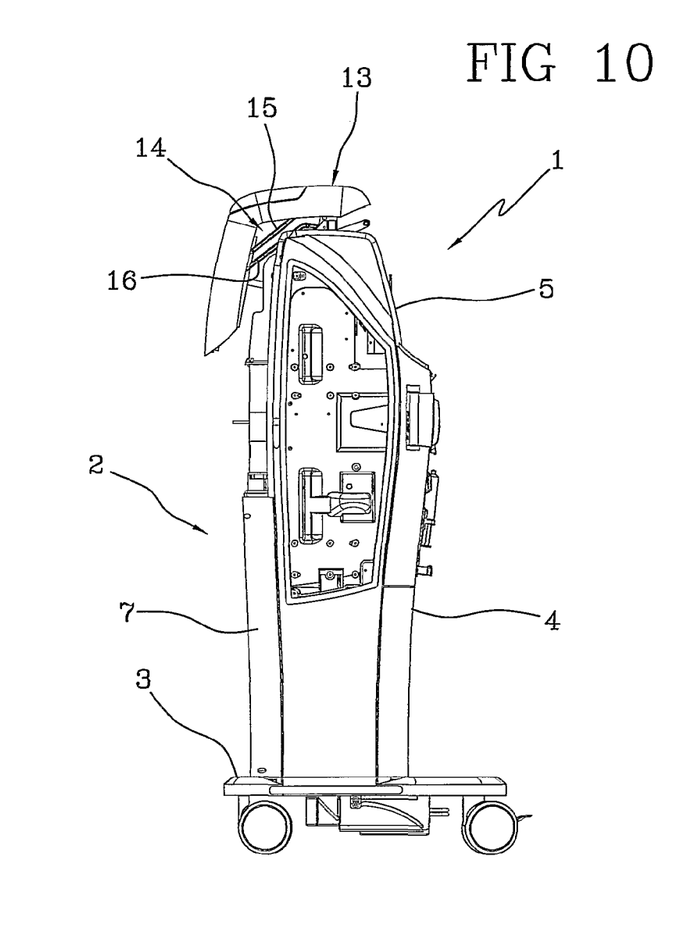
FIG. 10 is a side elevation of the apparatus of FIG. 9.

In the embodiment of the attached figures, cinematic coupling means 14 are operatively interposed between the cabinet and the user interface support body for moving the user interface from said first to said second position according to a prefixed trajectory. In other words, at least the movement from said first to said second position (and vice versa from said second to said first position) occurs along a path which is imposed and predetermined by the coupling means 14. Several embodiments are possible for the cinematic coupling means. In the embodiment of the enclosed drawings the cinematic coupling means 14 comprises a first element 15, having a first end 15a pivotally engaged to the user interface 13 and a second end 15b pivotally engaged to the cabinet 2. In practice the ends 15b and 15a are respectively engaged to the cabinet and to the user interface either directly or via interposition of other elements as it will be herein after described in detail. The cinematic coupling means also comprises a second element 16, having a first end 16a pivotally engaged to the user interface 13 in position displaced from the first end 15a of the first element and a second end 16b pivotally engaged to the cabinet in a position spaced from the second end 15b of the first element. As shown in FIGS. 4 and 8, the first and second elements are levers and form a first articulated parallelogram 17. The first articulated parallelogram allows the user interface to move according to an arc-shaped trajectory from the first position (FIGS. 1 and 2) to the second position (FIGS. 3 and 4) where the user interface is positioned above the top of the cabinet 2. The coupling means also comprises a second articulated parallelogram 18 (FIG. 11), which is cooperating with the first parallelogram to allow movement of the user interface according to a pre-fixed trajectory from the first to the second position. The second articulated parallelogram comprises a third element 19 (a lever in the enclosed embodiment), having a first end 19a pivotally engaged to the user interface and a second end 19b pivotally engaged to the cabinet. The second articulated parallelogram 18 also presents a fourth element 20 (again in the form of a lever), having a first end 20a, pivotally engaged to the user interface in a position displaced from the first end 19a of the third element, and a second end, pivotally engaged to the cabinet in a position spaced from the second end of the third element. The first and second articulated parallelograms operate in correspondence of respective opposite sides of the cabinet top portion, are identical in term of shape and length of the respective levers and are symmetrically engaged to the cabinet with respect to an axis of symmetry 21 which is vertical in the embodiment of the enclosed figures.

The levers of the articulated parallelograms could be substituted by alternative elements such as plates or bars interposed between the cabinet and the user interface in a way to define a prefixed path for the movement of the user interface between the first and the second position. While the solution adopting to articulated parallelograms each operating on a respective top side of the machine 1, a solution with one single, centrally positioned, articulated parallelogram could be envisaged.

Figure 11:
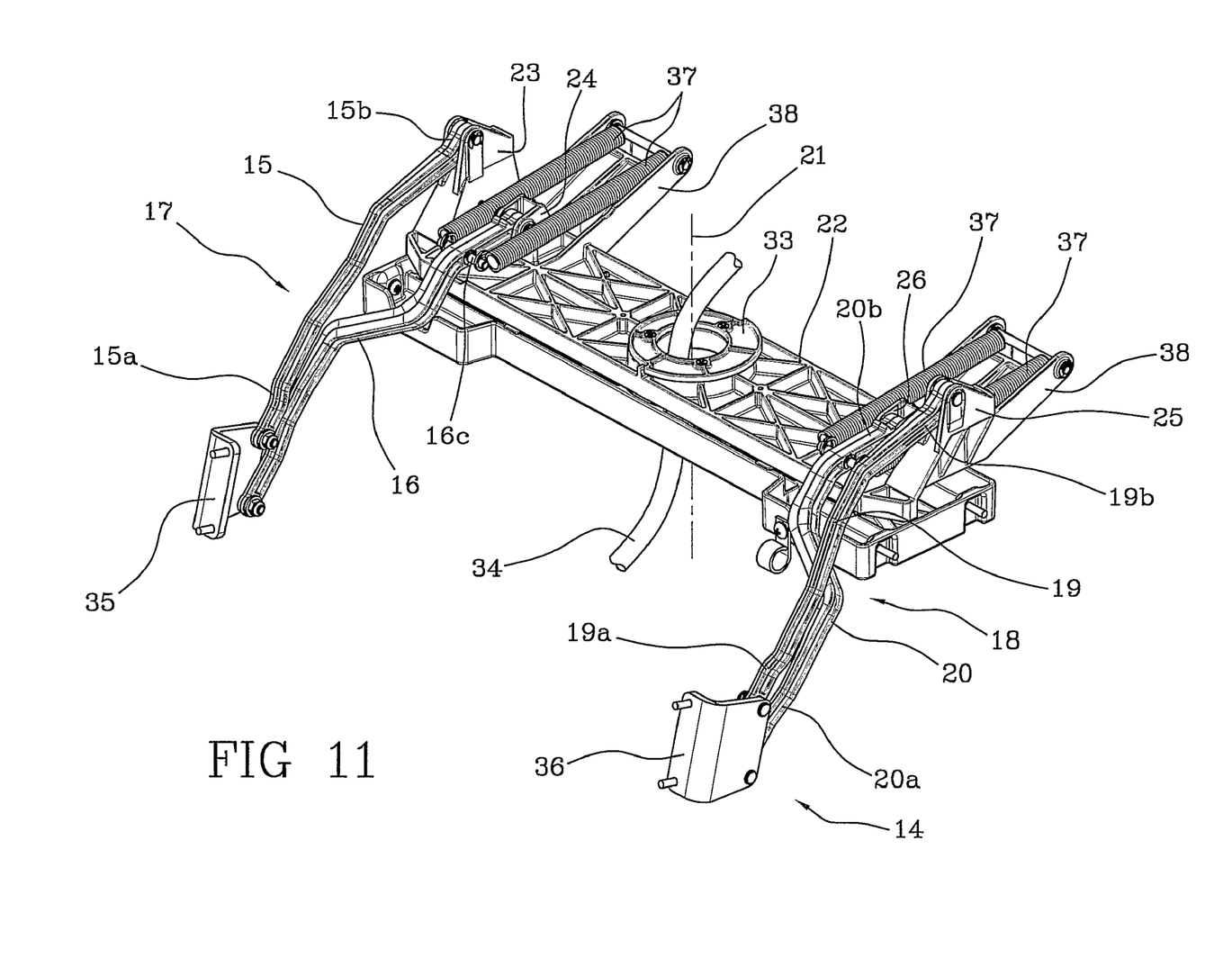
FIG. 11 is a particular of an embodiment of means for cinematically coupling the user interface to the cabinet of the blood processing apparatus, where for sake of clarity said means are represented separated from the remaining parts of the apparatus.

The coupling means can also include a rotating base 22 which is pivotally engaged to the cabinet around an axis of rotation (which is coincident to axis 21). In this case the second end 15b of the first lever is pivotally engaged to the rotating base. In practice according to the embodiment of the enclosed figures, the second end 15b is pivotally engaged to a projection 23 emerging from the rotating base 22. The second lever has a second end pivotally 16b engaged to the rotating base in a position spaced from the second end of the first lever in order to form the first articulated parallelogram which can rotate together with the rotating base. As shown in FIG. 11 also the second end 16b is pivotally engaged to a projection 24 emerging from the base 22.

Analogously the third and the fourth lever of the second articulated parallelogram have the respective second ends 19b and 20b pivotally engaged to the rotating base 22, for instance in correspondence of projections 25 and 26 emerging from the base 22.

Figure 12:
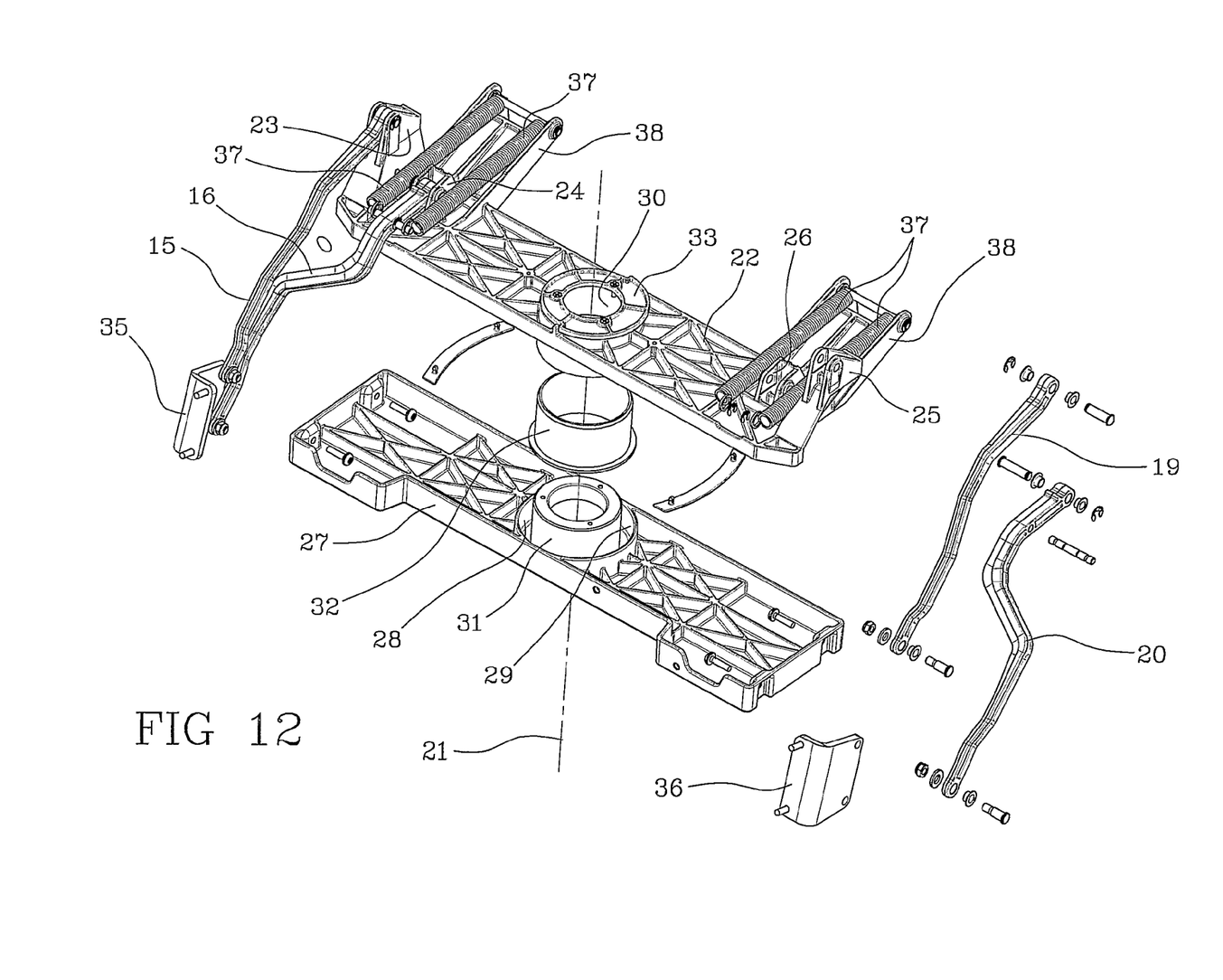
FIG. 12 is an exploded perspective view of the means of FIG. 11.

FIG. 12 in particular shows the non limiting constructive details of the coupling means 14 just described in general terms. As it shown in FIG. 12 a static body 27, which is substantially flat, is fixed to or directly obtained as part of the cabinet top 5 and the rotating base is hinged to the static body for rotation around said axis 21. The static body extends across the cabined along a horizontal direction above the top portion 6a of the housing 6 and includes a circular through passage 28 defining a tubular seat 29 at least partially receiving a mating tubular portion 30 of the rotating base 22. In the embodiment of FIGS. 11 and 12 the cabinet bears also a pivot member 31 coaxial to the seat 29 and defining an annual space where the tubular portion 30 and a bearing 32 are coaxially engaged. An axial lock ring 33 is also associated to the tubular portion 30 to axially keep together portion 30, bearing 32 and pivot 31. The described coupling between the tubular seat and the tubular portion allow rotation of the rotating base and define a passage for cables and wires 34. In detail as the user interface includes various parts (as for instance keys, knobs, toggles, screen) which need to be cabled to the control system and to the power supply system located in said interior housing, all cables connecting the control system and the power supply system to the user interface can pass through said passage in the rotating base. FIG. 11 and FIG. 12 also show that in the specific embodiment, the first ends 15a, 16a, 19a, 20a of the levers are in reality hinged to respective L-shaped plates 35 and 36 fixed to the user interface via conventional fasteners (such as screws, rivets, welding, gluing, etcetera).

Thanks to the rotating base the user interface has also a further degree of freedom as it can rotate around axis 21.

In the embodiment of the enclosed figures, however, the user interface presents side portions 106, transversely emerging from the support body 101 and interacting with the cabinet side wall top parts 5a for preventing rotation of the base until the latter has reached the second position above the cabinet. When reached said second position the user interface is entirely above the cabined and able to rotate around axis 21 to reach a third position angularly displaced with respect to the second position. In the enclosed figures it is shown an embodiment where the third position is angularly spaced by 180° as compared to the second position. Practically the third position is reached by rotating the interface by 180° around axis 21: the user interface in the third position is at the same height as in the second position but the screen faces the rear side of the apparatus. When the user interface has reached the third position it can be lowered again and moved from said third position to a fourth position where the user interface is approached again to the cabinet in a position different from said first position. More in detail, the coupling means allow to displace the user interface from said third to said fourth position by lowering the user interface according to a predetermined path. As for the movement between the first and second position also the movement between the third and fourth position occurs according a prefixed trajectory which is pre-defined and cannot be changed by the operator.

According to another aspect of the invention, the coupling means are so designed that during movement between the first and second position the user interface screen is kept substantially vertical and the seat 105 bottom wall 105a substantially horizontal. In this case substantially means that inclinations of ±20° with respect to the horizontal plane for the bottom wall 105a and with respect vertical plane for the user interface screen surface are deemed to be not relevant.

According to a further aspect of the present invention return means 37 are interposed between the cabinet and the movement means, for exerting a return force on the user interface attracting the user interface to stably position in one of the first, second, third or fourth positions.

The return means comprises at least one return spring (or other equivalent means able to exert a force when the interface is moved away from prefixed positions, such as a fluid actuated cylinder or a magnetic couple) which works between the coupling means and the cabinet to define a bi-stable condition for the user interface. In practice the spring tends to lower or to raise the user interface depending from the vertical position of the user interface relative to the cabinet. Therefore if an operator moves the user interface from first position to a position intermediate between the first and second positions, then the return spring will return the user interface to the first position or move the user interface to the second position. With an appropriate design choice of the springs and of the levers of the coupling means it is possible to customize the behavior of the coupling means and modify the dead point beyond which the spring tends to move the user interface to the second instead of to the first position. The same principle also applies to the movement between the third and forth position.

In the enclosed embodiment, two return springs of the helicoidal type are provided with, each spring having one end engaged to the cabinet (in correspondence of the engagement projection 38 fixed to the cabinet top portion) and one end engaged to the one of the levers of each articulated parallelogram (in the embodiment of FIGS. 11 and 12) levers 16 and 20 have an intermediate portion provided with a respective pin 16c, 20c for engaging the spring end).

The user interface can also be locked in one or more of the first, second, third and fourth position. In the embodiment of the enclosed drawings a lock mechanism is provided on the top portion of the cabinet to lock the user interface in the first position. Only when the lock is unlocked the user interface can move as above described.

The apparatus of the present invention can also present alternatives to what above described by way of non limiting example.

Indeed in view of the structure of the coupling means shown in the enclosed figures an operator shall manually move the user interface through its various position (though the return means assist the operator). Alternatively it is possible to provide the apparatus 1 with actuators (hydraulic, pneumatic or electric) which can act to automatically move the user interface through the various positions, for instance acting on one or more of the levers 15,16,19,20 and on the rotating base 22.

In any case the user interface shall be guided to follow a pre-determined path at least when moving from the first to the second position and vice-versa; in case a third and fourth positions are envisaged (as in the enclosed embodiment) the path followed by the user interface in the movement between the third and fourth positions shall be prefixed too. Clearly also the first, second and/or third and fourth positions are pre-fixed relative to the cabinet structure.

It should be noted that the specific coupling means above described which allow the user interface to move according to a predetermined path (which cannot be modified by the user) is a concept which could work per se, i.e. irrespective from the features relating to the fact that during its movement the user interface opens and closes the aperture 6a. Alternative type of cinematic couplings could also be envisaged.

For instance the coupling means could comprise a hinge coupling (an horizontal or a vertical hinge could be used), for instance arranged between a periphery of the user interface and the cabinet, so as to move the user interface as a sort of door according to a pre-determined trajectory for opening/ closing the access to the housing interior and orienting the screen according to a prefixed rotating path.

According to a further alternative the coupling means comprises a slide coupling arranged between the user interface and the cabinet to slidingly move the user interface according to a pre-fixed path (for instance a vertical or horizontal slide coupling could be envisaged) with respect to the cabinet and thereby and opening and closing the aperture in the cabinet top portion.

A combination of slides and hinges could also be envisaged.

The invention claimed is:

1. A blood processing apparatus comprising a cabinet (2), a user interface (13), and cinematic coupling means (14), the cabinet (2) defining at least an interior housing (6), the cabinet presenting an aperture (6a) for allowing access from outside into said housing, the user interface (13) being mounted on the cabinet, said user interface being movable from a first position, where the user interface closes said aperture and prevents access through said aperture into said housing, and a second position, where said aperture is not closed by said user interface so that access through said aperture into said housing is permitted, said user interface comprising a display screen, said cinematic coupling means (14) being interposed between the cabinet and the user interface (13) and being operative to move the user interface along a prefixed arc-shaped trajectory from said first position to said second position, said display screen being viewable by a user looking horizontally (a) when the user interface is in the first position, (b) when the user interface is in the second position, and (c) during the entire movement of the user interface from the first position to the second position.

2. Apparatus according to claim 1, wherein the cinematic coupling means (14) comprises at least a first element (15) having a first end pivotally engaged to the user interface and a second end pivotally engaged to the cabinet.

3. Apparatus according to claim 2, wherein the cinematic coupling means (14) comprises at least a second element (16) having a first end pivotally engaged to the user interface in position displaced from the first end of the first element, and a second end pivotally engaged to the cabinet in a position spaced from the second end of the first element, said first and second element elements forming a first articulated parallelogram.

4. Apparatus according to claim 3, wherein the cinematic coupling means (14) comprises at least a third element (19) having a first end pivotally engaged to the user interface and a second end pivotally engaged to the cabinet.

5. Apparatus according to claim 4, wherein the cinematic coupling means (14) comprises at least a fourth element (20) having a first end pivotally engaged to the user interface in position displaced from the first end of the third element, and a second end pivotally engaged to the cabinet in a position spaced from the second end of the third element, said third and fourth elements forming a second articulated parallelogram.

6. Apparatus according to claim 5, wherein the first and second articulated parallelograms operate in correspondence of respective opposite sides of the cabinet.

7. Apparatus according to claim 5, wherein the first and second articulated parallelograms are identical and symmetrically engaged to the cabinet.

8. Apparatus according to claim 1, wherein the cinematic coupling means (14) comprises a rotating base (22) which is pivotally engaged to the cabinet (2) around an axis of rotation (21) and which bears the user interface (13), the rotating base allowing rotation of the user interface around said axis to bring the user interface to a third position distinct from said first and second positions.

9. Apparatus according to claim 8, wherein the cinematic coupling means (14) includes at least a first element (15) having a first end pivotally engaged to the user interface and a second end pivotally engaged to the rotating base.

10. Apparatus according to claim 9, wherein the cinematic coupling means comprises (14) at least a second element (16) having a first end pivotally engaged to the user interface in position spaced from the first end of the first element, and a second end pivotally engaged to the rotating base in a position spaced from the second end of the first element, said first and second elements forming a first articulated parallelogram.

11. Apparatus according to claim 10, wherein the cinematic coupling means comprises at least a third element having a first end pivotally engaged to the user interface and a second end pivotally engaged to the rotating base.

12. Apparatus according to claim 11, wherein the cinematic coupling means comprises at least a fourth element having a first end pivotally engaged to the user interface in position spaced from the first end of the third element, and a second end pivotally engaged to the cabinet in a position spaced from the second end of the third element, said first third and fourth elements forming a second articulated parallelogram.

13. Apparatus according to claim 12, wherein the first and second articulated parallelograms operate in correspondence of respective opposite sides of the cabinet.

14. Apparatus according to claim 8, wherein the base comprises a tubular portion (30) coaxial to said axis (21) and engaging a corresponding tubular and coaxial mating portion (28) carried by the cabinet, said tubular portions allowing pivoting of the rotating base and defining a passage.

15. Apparatus according to claim 1, wherein the cabinet presents a box-like structure having a base portion (3), a main body (4) vertically extending from said base and a top portion (5) extending above said main body and wherein the user interface is positioned in correspondence of said top portion.

16. Apparatus according to claim 8, wherein the user interface (13) in said second position is entirely above said cabinet and able to rotate around said axis (21) to reach the third position angularly spaced with respect to the second position.

17. Apparatus according to claim 16, wherein the user interface (13) can be moved from said third position to a fourth position where the user interface is approached again to the cabinet in a position different from said first position.

18. Apparatus according to claim 17, wherein the third position is 180° angularly spaced with respect to the second position and wherein the coupling means (14) allow to displace the user interface (13) from said third to said fourth position by lowering the user interface according to a predetermined path.

19. Apparatus according to claim 1, wherein the user interface (13) comprises a support body (101) engaging the coupling means, and wherein the display screen (100) is mounted on the support body.

20. Apparatus according to claim 19, wherein the support body (101) presents an L-shaped profile and comprises a first portion (103) receiving the display screen and a second portion (104), transversal to the first portion, defining a receptacle area (105) on the top of the cabinet.

21. Apparatus according to claim 19, wherein the user interface presents side portions (106), interacting with the cabinet side walls and preventing rotation at least during part of the movement between the first and the second position.

22. Apparatus according to claim 1, comprising return means (37), interposed between the cabinet and the user interface for exerting a force on the user interface directed and oriented towards said cabinet.

23. Apparatus according to claim 22, wherein the return means comprises at least one return spring having one end engaged to the cabinet and one end engaged to the cinematic coupling means.

24. Apparatus according to claim 14, comprising a control system (11) located at least in part in said interior housing and cables (34) connecting the control system to the user interface, said cables passing through said passage in the rotating base (22).

25. Apparatus according to claim 24, wherein said part of the control system is seated in a top portion (6a) of said housing.

26. Apparatus according to claim 1, comprising an hydraulic circuit for the preparation of liquid to be used by the apparatus and for the discharge of waste liquid, the hydraulic circuit being housed in said housing below a control system circuitry.

27. Apparatus according to claim 1, wherein the cabinet presents at least an access (7) for inspecting a hydraulic circuit, said access being obtained on one wall selected from the group consisting of: a left side cabinet wall, a right side cabinet wall, a rear cabinet wall.

28. Apparatus according to claim 2, wherein the cinematic coupling means comprises a hinge coupling arranged between a periphery of the user interface and the cabinet, said hinge having an axis of rotation which is either horizontal or vertical.

29. Apparatus according to claim 2, wherein the cinematic coupling means comprises a slide coupling arranged between the user interface and the cabinet.

30. The apparatus of claim 1, wherein the orientation, with respect to vertical, of the display screen at the first position is within ±20° inclination of the orientation, with respect to vertical, of the display screen at the second position.

* * * * *

UNITED STATES PATENT AND TRADEMARK OFFICE
CERTIFICATE OF CORRECTION

| | | |
|---|---|---|
| PATENT NO. | : 7,935,250 B2 | Page 1 of 1 |
| APPLICATION NO. | : 12/373855 | |
| DATED | : May 3, 2011 | |
| INVENTOR(S) | : Michele Castellano et al. | |

It is certified that error appears in the above-identified patent and that said Letters Patent is hereby corrected as shown below:

At column 7, line 58, after "second" and before "elements" please delete "element".

At column 8, line 38, after "said" please delete "first".

At column 9, line 3, after "screen" and before "is" please delete "(100)".

Signed and Sealed this
Fifth Day of July, 2011

David J. Kappos
*Director of the United States Patent and Trademark Office*